United States Patent

Funatsu

[11] Patent Number: 5,622,693
[45] Date of Patent: Apr. 22, 1997

[54] SOLID COSMETIC COMPOSITION

[75] Inventor: Shinichiro Funatsu, Yokohama, Japan

[73] Assignee: Shiseido Company Ltd., Tokyo, Japan

[21] Appl. No.: 431,384

[22] Filed: Apr. 28, 1995

Related U.S. Application Data

[63] Continuation of Ser. No. 220,473, Mar. 31, 1994, abandoned, which is a continuation of Ser. No. 559,005, Jul. 27, 1990, abandoned.

[30] Foreign Application Priority Data

Aug. 7, 1989 [JP] Japan .................................. 1-204488

[51] Int. Cl.$^6$ ........................................ A61K 1/00
[52] U.S. Cl. ...................... 424/69; 424/401; 424/78.02; 424/78.03; 514/844
[58] Field of Search ................ 424/401, 69, 78.02, 424/78.03; 514/844

[56] References Cited

U.S. PATENT DOCUMENTS

| | | | |
|---|---|---|---|
| 3,939,260 | 2/1976 | Lafon | 434/401 |
| 4,178,695 | 12/1979 | Erbeia | 34/5 |
| 4,416,873 | 11/1983 | Puchalski et al. | 424/69 |
| 4,847,074 | 7/1989 | Hatae et al. | 514/844 |
| 5,087,446 | 2/1992 | Suzuki et al. | 424/69 |

FOREIGN PATENT DOCUMENTS

| | | |
|---|---|---|
| 0308238 | 9/1988 | European Pat. Off. |
| 2068447 | 11/1969 | France. |
| 2004182 | 8/1978 | United Kingdom. |

*Primary Examiner*—Amy Hulina
*Attorney, Agent, or Firm*—Sprung Horn Kramer & Woods

[57] ABSTRACT

A solid cosmetic composition comprising a freeze-dried product of an aqueous solution containing at least a water-soluble substance which is solid at normal temperature, and a water-soluble polymer as a thickener or a humectant, which solid cosmetic composition is used after being dissolved in a solvent.

5 Claims, No Drawings

SOLID COSMETIC COMPOSITION

This application is a continuation of application Ser. No. 08/220,473, filed on Mar. 31, 1994 now abandoned, which is a continuation of application Ser. No. 07/559,005 filed on Jul. 27, 1990 now abandoned.

BACKGROUND OF THE INVENTION

1. Field of the Invention

The present invention relates to a solid cosmetic composition. More specifically, it relates to a solidified cosmetic composition having a good solubility in water, feeling during use, high humectant effect, and free from thermal degradation.

2. Description of the Related Art

Heretofore, as solid cosmetics of the type used as a solution when applied, generally well known in the art are those prepared by formulating a chemical which provides an aesthetically pleasing depigmentation or a good skin activating effect, pulverizing the formulation by spray drying or pulverizing mixing, and further, granulating the composition. Nevertheless, many problems remained to be solved in the solid cosmetic prepared according to this method. For example, a problem arises in the solid cosmetic prepared by spray drying in that a thermal degradation of the chemical and the base occur due to heat applied during the spray drying, Also, when an excipient, a fluidizing agent and the like are added, to improve the miscibility and filling characteristics of the powder, the water solubility is lowered. Further, when a water-soluble polymer is formulated, to increase the humectant effect or improve the feeling when used as a cosmetic, i.e., for improving the body and health, undissolved powder lumps are often formed during the dissolution in water, and a problem arises in that it can be uniformly redissolved only with difficulty.

SUMMARY OF THE INVENTION

Accordingly, the objects of the present invention are to eliminate the above-mentioned disadvantages of the prior art and to provide a solid cosmetic composition having an excellent solubility in water, a good feeling during use, with a good body and a good effect on the skin, a high humectancy, and free from thermal degradation.

Other objects and advantages of the present invention will be apparent from the following description.

In accordance with the present invention, there is provided a solid cosmetic composition comprising a freeze-dried product of an aqueous solution containing at least a water-soluble substance which is solid at normal temperature, and a water-soluble polymer as a thickener or a humectant, wherein the solid cosmetic composition is used after being dissolved in a solvent.

DESCRIPTION OF THE PREFERRED EMBODIMENT

The present invention is described in more detail as follows.

The water-soluble substance, which is solid at normal temperature, comprises at least one of polyethers, monosaccharides, oligosaccharides, and polyhydric alcohols.

Examples of preferable polyethers include polyethylene glycols such as PEG-20000, PEG-9000, PEG-6000, PEG-4000 and the like, polypropylene glycols, polyethylene glycol-polypropylene glycol block copolymers or derivatives thereof; examples of preferable monosaccharides include D-xylose, D-ribose, D-arabinose, D-glucose, D-galactose, D-mannose, hepturose. 2-deoxy-D-ribose, 6-deoxy-L-mannose(L-rhamnose), D-glucosamine-(2-amino-2-deoxy-D-glucose), D-galactosamine-(2-amino-2-deoxy-D-galactose), sialic acid (neuramic acid), aminouronic acid, and D-glucronic acid; examples of preferable oligosaccharides include sucrose, lactose, α, α-trehalose, and raffinose; and an example of a preferable polyhydric alcohol is D-mannitol.

All of the water-soluble substances usable in the present invention preferably have a melting point of 40° C. or more.

The amount of the above-mentioned water soluble substance formulated is preferably 10 to 99% by weight of the solid cosmetic composition of the present invention. When the formulation amount is less, the amount of the above-mentioned water-soluble polymer formulated must be increased and the composition becomes sticky or slimy. Accordingly, the amount formulated is more preferably 70 to 99% by weight.

The water-soluble polymer usable as the thickening agent or the humectant in the present invention comprises at least one of vegetable natural polymers, microorganism natural polymers, polymers derived from animals, starch polymers, cellulose polymers, alginic acid polymers, polyvinyl polymers, acrylic polymers, polyethyleneimines, mucopoly-saccharides, and inorganic clay minerals.

Examples of preferable vegetable natural polymers usable in the present invention include gum arabic, gum tragacanth, galactan, guar gum, carageenan, pectin, quince seed, algae colloid (algae extract), starch (rice, corn, potato, wheat), and glycyrrhizinic acid; examples of preferable microorganism natural polymers include xanthan gum, dextran, succino glucan, and plullan; polymers of preferable polymers derived from animals include collagen or derivatives thereof, casein, albumin, and gelatin; examples of preferable starch polymers include carboxymethyl starch and methlhydroxypropyl starch; examples of preferable cellulose polymers include methyl cellulose, ethyl cellulose, methylhydroxypropyl cellulose, hydroxyethyl cellulose, sodium cellulose sulfate, hydroxypropyl cellulose, and sodium carboxymethyl cellulose (CMC); examples of preferable alignic acid polymers include sodium alginate, and alginic acid propylene glycol ester; examples of preferably polyvinyl polymers include polyvinyl alcohol, polyvinyl methyl ether, polyvinyl pyrrolidone, and carboxyvinyl polymer (Carbopol); examples of preferable acrylic acid polymers include sodium polyacrylates; examples of preferable mucopolysacchrides include hyaluronic acid, sodium hyaluronate, chondroitin sulfuric acid, sodium chondroitin sulfate, dermatan sulfuric acid, sodium dermatan sulfate, heparan sulfuric acid, and sodium heparan sulfate; and examples of preferable clay minerals include bentonite, aluminum magnesium silicate Veegum, Laponite, hectorite, anhydrous silic acid, and saponite.

The above-mentioned water-soluble polymer is preferably formulated in an amount of 1 to 90% by weight, in the solid cosmetic of the present invention. When the amount formulated is too large, the composition may be come sticky or slimy, and further the rate of dissolution in water become slower, and therefore, most preferably the amount of the above-mentioned water soluble polymer is 1 to 30% by weight.

In the present invention, if necessary, additives which are solid at normal temperature may be also formulated within a range which does not interfere with the effect of the present invention, such as humectants, surfactants, antioxidants, preservatives, sterilizers, amino acids, sequestering agents, vitamins, plant extracts, animal extracts, dyes, and UV-ray absorbents and the like. These additives are useful as cosmetics, and are solid at normal temperature after freeze drying.

The solid cosmetic composition of the present invention can be prepared by formulating the above-mentioned water-soluble substance and the above-mentioned water-soluble polymer in preferable amounts, dissolving the formulation in, for example, deinoized water, filling a predetermined amount thereof in a vesel of glass or resin, freezing by cooling to −40° C. or lower, and subsequently, drying by sublimation under a reduced pressure in a vacuum of, for example, 0.5 Torr or lower. The concentration of the raw solution dissolved in deionized water is preferably 15% by weight of the solids, from the standpoint of the water solubility.

The resultant freeze-dried composition is dissolved in the solvent such as deionized water or any mixture of deionized water with one or more of lower aliphatic alcohols such as ethanol, propanol, i-propanol, butanol and the like. The preferable alcohol content in the mixture is 50% by weight or less, preferably 15% by weight or less, preferably in an amount of 0.5 to 10 parts by weight per 100 parts by weight of the solvent.

The solid cosmetic composition of the present invention is preferably formulated in, for example, a white powder, humectant powder, pimple preventive, suntan preventive sunscreen, suntan products, hair growth agent, and dandruff/itch preventive.

According to the present invention, chemicals unstable in heat or water can be maintained in a stable condition for a long time, to thereby provide a solid cosmetic composition having an excellent water solubility, good feeling during use, with a good body and good effect on the skin, a high humectancy, and free from thermal degradation.

EXAMPLES

The present invention will now be further illustrated by, but is by no means limited to, the following Examples.

EXAMPLE 1, COMPARATIVE EXAMPLES 1, 2

Water-soluble polymers and water-soluble substances were formulated as shown in Table 1, and dissolved in deionized water to prepare formulated raw solutions. The formulated raw solutions were freeze dried to −40° C., vacuum dried in a conventional manner to obtain solid cosmetic compositions, and the appearance, feeling during use, and water solubility thereof were evaluated. The water solubility was evaluated by dissolving 0.5 g of the solid cosmetic composition in 5 ml of deionized water. The evaluation standards were as follows:

⊙ . . . good
○ . . . normal
Δ . . . not good
x . . . poor

TABLE 1

| | Water-soluble polymer | | Water-soluble substance | Deionized | Water | | Feeling | |
| --- | --- | --- | --- | --- | --- | --- | --- | --- |
| | Quince seed | Xanthan gum | PEG 9000 | water | solubility | Appearance | during use | |
| Example 1 | 1.0 wt % | 1.0 wt % | 8.0 wt % | 90.0 wt % | Quickly dissolved | ⊙ Crunchy porous cake | ⊙ With body, smooth and wet | ○ |
| Comparative Example 1 | 1.0 wt % | 1.0 wt % | — | 98.0 wt % | Undissolved powder lump of water-soluble polymer remains | Δ Fluffy cotton | Δ Slimy during coating and sticky after coating | Δ |
| Comparative Example 2 | — | — | 8.0 wt % | 92.0 wt % | Quickly dissolved | ⊙ Frmish porous cake | ○ Watery, without body | X |

As apparent from Table 1, the water solubility of Example 1 was good, and the appearance was of a crunchy, porous cake, which was bulky and pleasing to the eye, and further, the feeling during use was excellent with an adequate body, smooth spreading, and wet feeling. In Comparative Example 1, the results of all of the water solubility, appearance and feeling during use, were not satisfactory, and in Comparative Example 2 in which a water-soluble thickener was not formulated, the composition was watery without body, and the feeling during use was very bad.

Accordingly the requirements for a good water solubility, appearance, and feeling during use were satisfied in the Examples, but were not all satisfied at the same time in the Comparative examples.

EXAMPLE 2

According to the present invention, a white powder and humectant powder were obtained The formulation examples are as shown below, and were obtained by stirring and dissolving the respective components shown in the formulation examples, filling appropriate amounts thereof in vials, freezing at −40° C., and vacuum drying in a conventional manner.

| Ingredient | Amount (wt %) |
| --- | --- |
| Formulation Example of White Powder: | |
| (1) Sodium carboxymethyl cellulose | 0.5 |
| (2) Xanthan gum | 0.5 |
| (3) PEG 6000 | 5.0 |
| (4) D-mannitol | 5.0 |
| (5) Sodium glutamate | 0.1 |
| (6) L-ascorbic acid | 3.0 |
| (7) L-ascorbic acid magnesium phosphate ester | 3.0 |
| (8) Monoammonium glycyrrhizinic acid | 0.05 |
| (9) Deionized water | 82.85 |

| Ingredient | Amount (wt %) |
|---|---|
| Formulation Example of Humectant Powder: | |
| (1) D-mannitol | 2.0 |
| (2) PEG 4000 | 6.0 |
| (3) Sucrose | 2.0 |
| (4) Pectin | 0.2 |
| (5) Algae colloid | 0.2 |
| (6) Sodium hyaluronate | 0.5 |
| (7) PCA-sodium salt | 0.5 |
| (8) Atherocollagen (2% aqueous solution) | 1.0 |
| (9) Placenta extract | 0.5 |
| (10) Deionized water | 87.1 |

I claim:

1. A solid cosmetic composition consisting essentially of a freeze-dried product of an aqueous solution containing (i) at least one water-soluble polyethylene glycol having a molecular weight of 9,000 to 20,000 and (ii) as a thickener or a humectant at least one water-soluble polymer selected from the group consisting of vegetable natural polymers, microorganism natural polymers, polymers derived from animals, starch polymers, cellulose polymers, alginic acid polymers, polyvinyl polymers, acrylic polymers, polyethyleneimines, mucopolysaccharides and inorganic clay minerals, said solid cosmetic composition being capable of use after being dissolved in a solvent, the content of the water-soluble polyethylene glycol and of the water-soluble polymer in the freeze-dried product being respectively 10 to 99% by weight and 90 to 1% by weight based upon the total weight of the freeze-dried product.

2. A solid cosmetic composition as claimed in claim 1, further comprising at least one component selected from the group consisting of humectant, surfactant, antioxidant, preservative, sterilization, amino acid, sequestering agent, vitamin, plant extract, animal extract, dye, and UV ray absorbent.

3. A solution in a solvent of a solid cosmetic composition according to claim 1.

4. A solution according to claim 3, wherein the solvent is selected from the group consisting of deionized water and mixtures thereof with a lower aliphatic alcohol.

5. A solution according to claim 4, wherein the ratio of the solid cosmetic composition to the solvent is 0.5 to 10 parts by weight per 100 parts by weight of the solvent.

* * * * *